United States Patent
Lin et al.

(10) Patent No.: US 9,062,338 B1
(45) Date of Patent: Jun. 23, 2015

(54) METHOD OF PRODUCING HUMAN-LIKE GLYCOSYLATION PATTERN USING CELLS DEFICIENT IN GLUTAMINE SYNTHASE, CMP-N-ACETYLNEURAMINIC ACID HYDROXYLASE AND/OR GLYCOPROTEIN ALPHA-1,3-GALACTOSYLTRANSFERASE

(71) Applicants: Nan Lin, St. Louis, MO (US); Henry J. George, St. Louis, MO (US); Joaquina Mascarenhas, St. Louis, MO (US); Trevor N. Collingwood, St. Louis, MO (US); Kevin J. Kayser, St. Louis, MO (US); Katherine Achtien, St. Louis, MO (US)

(72) Inventors: Nan Lin, St. Louis, MO (US); Henry J. George, St. Louis, MO (US); Joaquina Mascarenhas, St. Louis, MO (US); Trevor N. Collingwood, St. Louis, MO (US); Kevin J. Kayser, St. Louis, MO (US); Katherine Achtien, St. Louis, MO (US)

(73) Assignee: SIGMA-ALDRICH CO. LLC, St. Louis, MO (US)

( * ) Notice: Subject to any disclaimer, the term of this patent is extended or adjusted under 35 U.S.C. 154(b) by 0 days.

(21) Appl. No.: 14/609,603

(22) Filed: Jan. 30, 2015

Related U.S. Application Data (62) Division of application No. 13/538,825, filed on Jun. 29, 2012, now Pat. No. 8,980,583.

(60) Provisional application No. 61/503,436, filed on Jun. 30, 2011.

(51) Int. Cl.
*C12P 21/00* (2006.01)

(52) U.S. Cl.
CPC .................................. *C12P 21/005* (2013.01)

(58) Field of Classification Search
None
See application file for complete search history.

*Primary Examiner* — Kagnew H Gebreyesus
(74) *Attorney, Agent, or Firm* — Polsinelli PC

(57) ABSTRACT

The present invention provides non-human mammalian cell lines that are deficient in CMP-Neu5Ac hydroxylase (Cmah) and/or glycoprotein alpha-1,3-galactosyltransferase (Ggta1). Also provided are methods for using the cells disclosed herein for producing recombinant proteins with human-like patterns of glycosylation.

11 Claims, 2 Drawing Sheets

METHOD OF PRODUCING HUMAN-LIKE GLYCOSYLATION PATTERN USING CELLS DEFICIENT IN GLUTAMINE SYNTHASE, CMP-N-ACETYLNEURAMINIC ACID HYDROXYLASE AND/OR GLYCOPROTEIN ALPHA-1,3-GALACTOSYLTRANSFERASE

CROSS REFERENCE TO RELATED APPLICATIONS

This application is a divisional application of U.S. patent application Ser. No. 13/538,825, filed Jun. 29, 2012, which claims the priority of U.S. provisional application No. 61/503,436, filed Jun. 30, 2011, each of which is hereby incorporated by reference in its entirety.

FIELD OF THE INVENTION

The present disclosure generally relates to cells useful for the production of proteins and, in particular therapeutic proteins. More specifically, the present disclosure relates to cells deficient in certain N-glycan processing enzymes, methods for producing the cells, and methods for using the cells to generate proteins having certain glycosylation patterns.

BACKGROUND OF THE INVENTION

Approximately 70% of therapeutic proteins such as antibodies, growth factors, cytokines, hormones, and clotting factors are glycoproteins, which are proteins modified post-translationally by the attachment of glycans. Most recombinant therapeutic glycoproteins are produced in mammalian expression systems because the location, number, and structure of N-glycans have been shown to affect the bioactivity, solubility, stability, pharmacokinetics, immunogenicity, and clearance rate of therapeutic glycoproteins. Two differences in the protein glycosylation machinery of humans and other mammals account for differences in the glycosylation patterns of glycoproteins produced by human cells and glycoproteins produced by other mammalian cells such as rodent cells.

First, humans cannot synthesize a terminal galactose-alpha-1,3-galactose moiety (also known as alpha-Gal or α-Gal) on N-glycans. The enzyme glycoprotein alpha-1,3-galactosyltransferase (Ggta1) forms the α-Gal moiety by linking a galactose residue via an α-1,3 gycosidic bond to a terminal galactose of the N-glycan. Humans apparently have a GGTA1 gene, but it is an expressed pseudogene encoding a non-functional truncated protein containing the first four translated exons but missing the two catalytic exons. Even though humans do not express a functional Ggta1 enzyme and, therefore, do not synthesize α-Gal moieties many humans produce antibodies against this structure.

Second, humans cannot synthesize the sialic acid, N-glycolylneuraminic acid (Neu5Gc). Neu5Gc is produced by the hydroxylation of CMP-N-acetylneuraminic acid (Neu5Ac) to CMP-Neu5Gc by the enzyme CMP-Neu5Ac hydroxylase (Cmah). Although the human CMAH gene is irreversibly mutated, preventing the expression of Neu5Ac, traces of Neu5Gc have been detected in human serum. It appears that nonhuman Neu5Gc can be metabolically incorporated into human tissues from certain mammalian-derived foods, such that essentially all humans have Neu5Gc-specific antibodies, sometimes at high levels.

Chinese Hamster Ovary (CHO) cells are widely used for the manufacture of protein therapeutics, in part because they were assumed to produce proteins with human-like glycosylation patterns. For example, it was generally accepted that CHO cells lack the biosynthetic machinery to produce glycoproteins with α-Gal moieties. Moreover, even though CHO cells express Cmah and produce proteins having Neu5Gc units, the ratio of Neu5Gc to Neu5Ac units can be reduced by modifying CHO cell culture conditions. Despite the general acceptance that CHO cells were unable to synthesize α-Gal moieties, the CHO ortholog of Ggta1 has recently been identified (Bosques et al. Nature Biotechnol., 2010, 28(11):1153-1156). Because of the potential for hypersensitive reactions to recombinant therapeutic glycoproteins, there is a need for CHO cell lines and other non-human mammalian cell lines that produce glycoproteins devoid of α-Gal and/or Neu5Gc residues.

SUMMARY OF THE INVENTION

Briefly, therefore, one aspect of the present disclosure provides a non-human mammalian cell line deficient in cytidine monophosphate-N-acetylneuraminic acid hydroxylase (Cmah). In one embodiment, the cell line comprises an inactivated chromosomal sequence encoding Cmah. In certain embodiments, the inactivated chromosomal sequence encoding Cmah comprises a deletion of at least one nucleotide, an insertion of at least one nucleotide, a substitution of at least one nucleotide, or combinations thereof. In one embodiment, the inactivated chromosomal sequence encoding Cmah comprises no exogenously introduced sequence. In another embodiment, the inactivated chromosomal sequence encoding Cmah is monoallelic and the cell line produces a reduced amount of Cmah. In yet another embodiment, the inactivated chromosomal sequence encoding Cmah is biallelic and the cell line produces no Cmah. In one embodiment, the chromosomal sequence is inactivated with a targeting endonuclease, for example, a meganuclease, a TALEN, a site-specific endonuclease, or a zinc finger nuclease. In any of these embodiments, the cell line can produce proteins that lack N-glycolylneuraminic acid (Neu5Gc) residues.

In another aspect of the present disclosure, the cell line deficient in Cmah is also deficient in Ggta1. In one embodiment of this cell line, the cell line comprises an inactivated chromosomal sequence encoding Ggta1. In certain embodiments, the inactivated chromosomal sequence encoding Ggta1 comprises a deletion of at least one nucleotide, an insertion of at least one nucleotide, a substitution of at least one nucleotide, or combinations thereof. In one embodiment, the inactivated chromosomal sequence encoding Ggta1 comprises no exogenously introduced sequence. In one embodiment, the inactivated chromosomal sequence encoding Ggta1 is monoallelic and the cell line produces a reduced amount of Ggta1. In another embodiment, the inactivated chromosomal sequence encoding Ggta1 is biallelic and the cell line produces no Ggta1. In another embodiment, the chromosomal sequence is inactivated with a targeting endonuclease, for example, a meganuclease, a TALEN, a site-specific endonuclease, or a zinc finger nuclease. In any of these embodiments, the non-human mammalian cell line can produce proteins that additionally lack galactose-alpha-1,3-galactose (alpha-Gal) residues.

In one embodiment, the cell line comprises a monoallelic inactivation of the chromosomal sequence encoding Cmah and a monoallelic inactivation of the chromosomal sequence encoding Ggta1, and the cell line produces a reduced amount of Cmah and a reduced amount of Ggta1. In another embodiment, the cell line comprises a biallelic inactivation of the chromosomal sequence encoding Cmah and a biallelic inactivation of the chromosomal sequence encoding Ggta1, and the cell line produces no Cmah or Ggta1. In a particular embodiment, the non-human mammalian cell line produces proteins that lack N-glycolylneuraminic acid (Neu5Gc) residues and galactose-alpha-1,3-galactose (alpha-Gal) residues.

In a particular embodiment of the invention, the cell line is a Chinese hamster ovary (CHO) cell line. In one embodiment, the CHO cell line comprises a monoallelic inactivation of the chromosomal sequence encoding Cmah, and produces a reduced amount of Cmah. In another embodiment, the CHO cell line comprises a biallelic inactivation of the chromosomal sequence encoding Cmah, and produces no Cmah. In another embodiment, the CHO cell line comprises a monoallelic inactivation of the chromosomal sequence encoding Cmah and a monoallelic inactivation of the chromosomal sequence encoding Ggta1, and produces a reduced amount of Cmah and a reduced amount of Ggta1. In yet another embodiment, the CHO cell line comprises a biallelic inactivation of the chromosomal sequence encoding Cmah and a biallelic inactivation of the chromosomal sequence encoding Ggta1, and produces no Cmah or Ggta1. In one embodiment, the CHO cell line produces proteins that lack N-glycolylneuraminic acid (Neu5Gc) residues and galactose-alpha-1,3-galactose (alpha-Gal) residues.

In another aspect, the disclosure encompasses methods for producing a cell line deficient in Cmah and/or Ggta1. In one embodiment, the method comprises introducing into the cell line a targeting endonuclease or a nucleic acid encoding a targeting endonuclease directed to a chromosomal sequence encoding Cmah. In another embodiment, the method comprises introducing into a cell line that is deficient in Cmah, a targeting endonuclease or a nucleic acid encoding a targeting endonuclease directed to a chromosomal sequence encoding Ggta1. In another embodiment, the method comprises introducing into a cell line a targeting endonuclease or a nucleic acid encoding a targeting endonuclease directed to a chromosomal sequence encoding Cmah and a targeting endonuclease or a nucleic acid encoding a targeting endonuclease directed to a chromosomal sequence encoding Ggta1.

Another aspect of the disclosure encompasses a method for producing a recombinant protein with a human-like glycosylation pattern. The method comprises expressing the protein in a non-human mammalian cell line deficient in Cmah and/or Ggta1. In one specific embodiment, the cell line is a Chinese hamster ovary (CHO) cell line. In one embodiment, the cell line comprises an inactivated chromosomal sequence encoding Cmah and/or an inactivated chromosomal sequence encoding Ggta1. In one embodiment, the inactivated chromosomal sequence encoding Cmah and/or Ggta1 is monoallelic and the cell line produces a reduced amount of Cmah and/or Ggta1. In another embodiment, the inactivated chromosomal sequence encoding Cmah and/or Ggta1 is biallelic, and the cell line produces no Cmah and/or Ggta1. In another embodiment, the recombinant protein lacks N-glycolylneuraminic acid (Neu5Gc) residues and/or galactose-alpha-1,3-galactose (alpha-Gal) residues. In one embodiment, the recombinant protein has at least one property that is improved relative to a similar recombinant protein produced by a comparable cell line not deficient in Cmah and/or Ggta1, for example, reduced immunogenicity, increased bioavailability, increased efficacy, increased stability, increased solubility, improved half-life, improved clearance, improved pharmacokinetics, and combinations thereof. The recombinant protein can be any protein, including a therapeutic protein. Exemplary proteins include those selected from an antibody, an antibody fragment, a growth factor, a cytokine, a hormone, a clotting factor, and functional fragment or variants thereof.

Other aspects and iterations of the disclosure are described in more detail below.

DETAILED DESCRIPTION OF THE INVENTION

The present disclosure provides non-human mammalian cell lines deficient in Cmah and/or Ggta1. In one embodiment, the cell lines comprise inactivated chromosomal sequences encoding Cmah and/or Ggta1 such that the cell lines produce reduced amounts of Cmah and/or Ggta1. In another embodiment, the cell lines comprise inactivated chromosomal sequences encoding Cmah and/or Ggta1 such that the cell lines produce no Cmah and/or Ggta1. Also provided herein are methods for making the cell lines disclosed herein and methods for using the cell lines disclosed herein to produce recombinant proteins with human-like patterns of glycosylation. Because the cell lines are deficient in Cmah and/or Ggta1, the cell lines produce recombinant glycoproteins with reduced Neu5Gc and/or α-Gal content or glycoproteins that lack Neu5Gc and/or α-Gal.

(I) Cell Lines Deficient in Cmah and/or Ggta1

One aspect of the present disclosure provides a non-human mammalian cell line deficient in cytidine monophosphate-N-acetylneuraminic acid hydroxylase (Cmah) and/or glycoprotein alpha-1,3-galactosyltransferase (Ggta1).

(a) Cmah and Ggta1

Cmah and Ggta1 are enzymes involved in the generation of N-glycans on glycoproteins. Cmah catalyzes the conversion of the sialic acid Neu5Ac to its hydroxylated derivative Neu5Gc. Ggta1 links a galactose residue via an α-1,3 glycosidic bond to a galactose on the N-glycan to form a terminal Gal-α-1,3-Gal (i.e., α-Gal) moiety. In one embodiment, the cell line is deficient in Cmah. In another embodiment, the cell line is deficient in Ggta1. In still another embodiment, the cell line is deficient in both Cmah and Ggta1.

In some instances, the cell line deficient in Cmah and/or Ggta1 may have reduced levels of Cmah and/or Ggta1 relative to the parental cell line. For example, the levels of Cmah and/or Ggta1 may be reduced from about 5% to about 10%, from about 10% to about 20%, from about 20% to about 30%, from about 30% to about 40%, from about 40% to about 50%, from about 50% to about 60%, from about 60% to about 70%, from about 70% to about 80%, from about 80% to about 90%, or from about 90% to about 99.9% relative to the parental cell line that is not deficient in Cmah and/or Ggta1. The cell line having reduced levels of Cmah and/or Ggta1 generally will produce proteins with reduced Neu5Gc and/or α-Gal content relative to proteins produced by comparable cells that are not deficient in Cmah and/or Ggta1.

In other instances, the cell line deficient in Cmah and/or Ggta1 may produce essentially no Cmah and/or Ggta1. As used herein, the term "essentially no Cmah and/or Ggta1" means that no Cmah and/or Ggta1 mRNA or protein can be detected in the deficient cells or lysates derived therefrom using procedures well known in the art. Non-limiting examples of suitable procedures for determining the level of mRNA or protein include PCR, qPCR, Western blotting, and ELISA assays. Thus, the level of Cmah and/or Ggta1 mRNA and/or protein detected in the deficient cells or lysates is essentially the same as background levels. The cell line devoid of Cmah and/or Ggta1 generally will produce proteins that lack Neu5Gc and/or α-Gal residues.

In some embodiments, the genome of the cell line deficient in Cmah and/or Ggta1 may be edited such that the chromosomal sequence encoding Cmah and/or the chromosomal sequence encoding Ggta1 is inactivated. As used herein, the term "inactivated chromosomal sequence" refers to a chromosomal sequence that is unable to generate a functional gene product. In one embodiment in which the cell line comprises euploid cells, the inactivated chromosomal sequence may be monoallelic such that the cell produces reduced levels of Cmah and/or Ggta1. In another embodiment in which the cell line is euploid, the inactivated chromosomal sequence may be biallelic such that the cell produces essentially no Cmah and/or Ggta1 and the cell may be termed a "knockout" cell. Alternatively, in other embodiments in which the cell line is aneuploid, one or more copies of the chromosomal sequence(s) encoding Cmah and/or Ggta1 is/are inactivated resulting in a reduced amount of Cmah and/or Ggta1. In another embodiment in which the cell line is aneuploid, all copies of the chromosomal sequence(s) encoding Cmah and/or Ggta1 are inactivated resulting in a complete loss of Cmah and/or Ggta1 gene expression.

The inactivated chromosomal sequence encoding Cmah and/or Ggta1 may comprise a deletion of at least one nucleotide, an insertion of at least one nucleotide, or a substitution of at least one nucleotide. The chromosomal sequence encoding Cmah and/or Ggta1 may be inactivated using targeting endonuclease-mediated genome editing technology as detailed below in section (II). In various embodiments, the chromosomal sequence encoding Cmah and/or Ggta1 may be inactivated by deletion of all or part of the exonic coding region, deletion of all or part of a control region, and/or deletion of a splice site such that the cell line is unable to produce Cmah and/or Ggta1. In other embodiments, the chromosomal sequence encoding Cmah and/or Ggta1 may be inactivated via deletions, insertions, and/or nucleotide substitutions to introduce a premature stop codon, new splice site, and/or SNPs into the chromosomal sequence such that the cell line is unable to produce Cmah and/or Ggta1.

In one embodiment, the cell line may comprise an inactivated chromosomal sequence encoding Cmah due to a deletion, insertion, and/or substitution of at least one nucleotide within the chromosomal sequence encoding Cmah. For example, the chromosomal sequence encoding Cmah may be inactivated due to a deletion, insertion, and/or substitution of at least one nucleotide within exon 5 of the chromosomal sequence encoding Cmah. In another embodiment, the cell line may comprise an inactivated chromosomal sequence encoding Ggta1 due to a deletion, insertion, and/or substitution of at least one nucleotide within the chromosomal sequence encoding Ggta1. For example, the chromosomal sequence encoding Ggta1 may be inactivated due to a deletion, insertion, and/or substitution of at least one nucleotide within exon 9 of the chromosomal sequence encoding Ggta1.

In some embodiments, the cell line deficient in Cmah and/or Ggta1 may also be deficient in glutamine synthase (GS), dihydrofolate reductase (DHFR), hypoxanthine-guanine phosphoribosyltransferase (HPRT), or combinations thereof. The cell line further comprising deficiencies in GS, DHFR, and/or HPRT may be deficient in GS, DHFR, and/or HPRT due to inactivated chromosomal sequences encoding GS, DHFR, and/or HPRT.

(b) Cell Types

The type of cell line that is deficient in Cmah and/or Ggta1 can be any of a number of suitable cell types. In general, the cell line is a non-human mammalian cell line. Suitable non-human mammalian cell lines include but are not limited to Chinese hamster ovary (CHO) cells, baby hamster kidney (BHK) cells; mouse myeloma NS0 cells, mouse embryonic fibroblast 3T3 cells, mouse B lymphoma A20 cells; mouse melanoma B16 cells; mouse myoblast C2C12 cells; mouse myeloma SP2/0 cells; mouse embryonic mesenchymal C3H-10T1/2 cells; mouse carcinoma CT26 cells, mouse prostate DuCuP cells; mouse breast EMT6 cells; mouse hepatoma Hepa1c1c7 cells; mouse myeloma J5582 cells; mouse epithelial MTD-1A cells; mouse myocardial MyEnd cells; mouse renal RenCa cells; mouse pancreatic RIN-5F cells; mouse melanoma X64 cells; mouse lymphoma YAC-1 cells; rat glioblastoma 9L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; rat monocyte/macrophage DH82 cells; monkey kidney SV-40 transformed fibroblast (COS7) cells; monkey kidney CVI-76 cells; and African green monkey kidney (VERO-76) cells. An extensive list of non-human mammalian cell lines may be found in the American Type Culture Collection catalog (ATCC, Mamassas, Va.). In one embodiment, the cell line that is deficient in Cmah and/or Ggta1 is other than a mouse cell line. In still another embodiment, the cell line that is deficient in Cmah and/or Ggta1 is other than a porcine cell line.

In some embodiments, the cell line is of a type that is widely used for the production of recombinant glycol proteins. In an exemplary embodiment, the cell line is a CHO cell line. Numerous CHO cell lines are available from ATCC and commercial vendors. Suitable CHO cell lines include, but are not limited to, CHO-K1 cells and derivatives thereof, CHO-K1SV cells, CHO DG44 cells, CHO-S cells, CHO P12 cells, CHO pro3$^-$ cells, CHO/DHFR$^-$ cells, CHO/GS$^-$, and CHO DXB11 cells.

(c) Optional Nucleic Acid

In some embodiments, the non-human mammalian cell line disclosed herein may further comprise at least one nucleic acid sequence encoding a recombinant protein. The recombinant protein may be, without limit, an antibody, a fragment of an antibody, a monoclonal antibody, a humanized antibody, a humanized monoclonal antibody, a chimeric antibody, an IgG molecule, an IgG heavy chain, an IgG light chain, an IgA molecule, an IgD molecule, an IgE molecule, an IgM molecule, a glycoprotein, a growth factor, a cytokine, an interferon, an interleukin, a hormone, a clotting (or coagulation) factor, a blood component, an enzyme, a therapeutic protein, a nutraceutical protein, a vaccine, a functional fragment or functional variant of any of the forgoing, or a fusion protein comprising any of the foregoing proteins and/or functional fragments or variants thereof.

In some embodiments, the nucleic acid sequence encoding the recombinant protein may be linked to a nucleic acid sequence encoding hypoxanthine-guanine phosphoribosyltransferase (HPRT), dihydrofolate reductase (DHFR), and/or glutamine synthase (GS), such that HPRT, DHFR, and/or GS may be used as an amplifiable selectable marker.

In some embodiments, the nucleic acid sequence encoding the recombinant protein may be extrachromosomal. That is, the nucleic acid encoding the recombinant protein may be transiently expressed from a plasmid, a cosmid, an artificial chromosome, a minichromosome, and the like. Those skilled in the art are familiar with suitable expression constructs, appropriate expression control sequences, and methods of introducing said constructs into cells.

In other embodiments, the nucleic acid sequence encoding the recombinant protein may be chromosomally integrated into the genome of the cell such that the recombinant protein is stably expressed. In some iterations of this embodiment, the nucleic acid sequence encoding the recombinant protein may be operably linked to an appropriate heterologous expression control sequence (i.e., promoter). In other iterations, the nucleic acid sequence encoding the recombinant protein may be placed under control of an endogenous expression control sequence. The nucleic acid sequence encoding the recombinant protein can be integrated into the genome of the cell line using well known techniques.

Methods, vectors, and cloning techniques for preparing and introducing exogenous nucleic acid sequences (e.g., those encoding a recombinant protein) are well-known in the art (see, e.g., "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., $3^{rd}$ edition, 2001).

(d) Exemplary Embodiments

In one specific embodiment, the cell line is a CHO cell line comprising a monoallelic or biallelic inactivation of the chromosomal sequence encoding Cmah. In another specific embodiment, the cell line is a CHO cell line comprising a monoallelic or biallelic inactivation of the chromosomal sequence encoding Ggta1. In still another embodiment, the cell line is a CHO cell line comprising a monoallelic or biallelic inactivation of the chromosomal sequence encoding Cmah and a monoallelic or biallelic inactivation of the chromosomal sequence encoding Ggta1.

(II) Methods for Preparing Cell Lines Deficient in Cmah and/or Ggta1

The cell line deficient in Cmah and/or Ggta1 can be prepared by a variety of methods. In certain embodiments, the cell line deficient in Cmah and/or Ggta1 can be prepared by a targeting endonuclease-mediated genome editing process. In other embodiments, the cell line deficient in Cmah and/or Ggta1 can be prepared by RNAi methods, random mutagenesis, site-specific recombination systems, or other methods known in the art.

(a) Targeting Endonuclease-Mediated Genome Editing

Targeting endonucleases can be used to edit (i.e., inactivate or modify) a specific chromosomal sequence. A specific chromosomal sequence can be inactivated by introducing into a cell a targeting endonuclease or a nucleic acid encoding the targeting endonuclease, which is engineered to target a specific chromosomal sequence. In one embodiment, the targeting endonuclease recognizes and binds the specific chromosomal sequence and introduces a double-stranded break that is repaired by a non-homologous end-joining (NHEJ) repair process. Because NHEJ is error prone, a deletion, insertion, or substitution of at least one nucleotide may occur, thereby disrupting the reading frame of the chromosomal sequence such that no protein product is produced. In another embodiment, the targeting endonucleases can also be used to edit a chromosomal sequence via a homologous recombination reaction by co-introducing a polynucleotide having substantial sequence identity with a portion of the targeted chromosomal sequence. The double-stranded break introduced by the targeting endonuclease is repaired by a homology-directed repair process such that the chromosomal sequence is exchanged with the polynucleotide in a manner that results in the chromosomal sequence being edited.

(i) Targeting Endonucleases

A variety of targeting endonucleases can be used to edit the chromosomal sequence. The targeting endonuclease may be a naturally-occurring protein or an engineered protein. In one embodiment, the targeting endonuclease may be a meganuclease. Meganucleases are endodeoxyribonucleases characterized by long recognition sequences, i.e., the recognition sequence generally ranges from about 12 base pairs to about 40 base pairs. As a consequence of this requirement, the recognition sequence generally occurs only once in any given genome. Among meganucleases, the family of homing endonucleases named LAGLIDADG has become a valuable tool for the study of genomes and genome engineering. A meganuclease may be targeted to a specific chromosomal sequence by modifying its recognition sequence using techniques well known to those skilled in the art.

In another embodiment, the targeting endonuclease may be a transcription activator-like effector (TALE) nuclease. TALEs are transcription factors from the plant pathogen *Xanthomonas* that can be readily engineered to bind new DNA targets. TALEs or truncated versions thereof may be linked to the catalytic domain of endonucleases such as FokI to create targeting endonuclease called TALE nucleases or TALENs.

In still another embodiment, the targeting endonuclease may be a site-specific endonuclease. In particular, the site-specific endonuclease may be a "rare-cutter" endonuclease whose recognition sequence occurs rarely in a genome. Preferably, the recognition sequence of the site-specific endonuclease occurs only once in a genome. In an alternate further embodiment, the targeting endonuclease may be an artificial targeted DNA double strand break inducing agent.

In other embodiments, the targeting endonuclease may be a zinc finger nuclease (ZFN). Typically, a zinc finger nuclease comprises a DNA binding domain (i.e., zinc finger) and a cleavage domain (i.e., nuclease), both of which are described below.

Zinc Finder Binding Domain.

Zinc finger binding domains can be engineered to recognize and bind to any nucleic acid sequence of choice. See, for example, Beerli et al. (2002) Nat. Biotechnol. 20:135-141; Pabo et al. (2001) Ann. Rev. Biochem. 70:313-340; Isalan et al. (2001) Nat. Biotechnol. 19:656-660; Segal et al. (2001) Curr. Opin. Biotechnol. 12:632-637; Choo et al. (2000) Curr. Opin. Struct. Biol. 10:411-416; Zhang et al. (2000) J. Biol. Chem. 275(43):33850-33860; Doyon et al. (2008) Nat. Biotechnol. 26:702-708; and Santiago et al. (2008) Proc. Natl. Acad. Sci. USA 105:5809-5814. An engineered zinc finger binding domain may have a novel binding specificity compared to a naturally-occurring zinc finger protein. Engineering methods include, but are not limited to, rational design and various types of selection. Rational design includes, for example, using databases comprising doublet, triplet, and/or quadruplet nucleotide sequences and individual zinc finger amino acid sequences, in which each doublet, triplet or quadruplet nucleotide sequence is associated with one or more amino acid sequences of zinc fingers which bind the particular triplet or quadruplet sequence. See, for example, U.S. Pat. Nos. 6,453,242 and 6,534,261, the disclosures of which are incorporated by reference herein in their entireties. As an example, the algorithm of described in U.S. Pat. No. 6,453, 242 can be used to design a zinc finger binding domain to target a preselected sequence. Alternative methods, such as rational design using a nondegenerate recognition code table may also be used to design a zinc finger binding domain to target a specific sequence (Sera et al. (2002) Biochemistry 41:7074-7081). Publically available web-based tools for identifying potential target sites in DNA sequences as well as designing zinc finger binding domains are known in the art. For example, tools for identifying potential target sites in DNA sequences can be found at zincfingertools.org. Tools for designing zinc finger binding domains can be found at bindr.gdcb.iastate.edu/ZiFiT/. (See also, Mandell et al. (2006) Nuc. Acid Res. 34:W516-W523; Sander et al. (2007) Nuc. Acid Res. 35:W599-W605.)

A zinc finger binding domain can be designed to recognize and bind a DNA sequence ranging from about 3 nucleotides to about 21 nucleotides in length, or preferably from about 9 to about 18 nucleotides in length. In general, the zinc finger binding domains of the zinc finger nucleases disclosed herein comprise at least three zinc finger recognition regions (i.e., zinc fingers). In one embodiment, the zinc finger binding domain comprises four zinc finger recognition regions. In another embodiment, the zinc finger binding domain comprises five zinc finger recognition regions. In still another embodiment, the zinc finger binding domain comprises six zinc finger recognition regions. A zinc finger binding domain can be designed to bind to any suitable target DNA sequence. See for example, U.S. Pat. Nos. 6,607,882; 6,534,261 and 6,453,242, the disclosures of which are incorporated by reference herein in their entireties.

Exemplary methods of selecting a zinc finger recognition region may include phage display and two-hybrid systems, which are described in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237, each of which is incorporated by reference herein in its entirety. In addition, enhancement of binding specificity for zinc finger binding domains has been described, for example, in WO 02/077227, the entire disclosure of which is incorporated herein by reference.

Zinc finger binding domains and methods for design and construction of fusion proteins (and polynucleotides encoding same) are known to those of skill in the art and are described in detail in, for example, U.S. Pat. No. 7,888,121, which is incorporated by reference herein in its entirety. Zinc finger recognition regions and/or multi-fingered zinc finger proteins can be linked together using suitable linker sequences, including for example, linkers of five or more amino acids in length. See, U.S. Pat. Nos. 6,479,626; 6,903,185; and 7,153,949, the disclosures of which are incorporated by reference herein in their entireties, for non-limiting examples of linker sequences of six or more amino acids in length. The zinc finger binding domain described herein may include a combination of suitable linkers between the individual zinc fingers of the protein.

In some embodiments, the zinc finger nuclease further comprises a nuclear localization signal or sequence (NLS). A NLS is an amino acid sequence which facilitates targeting the zinc finger nuclease protein into the nucleus to introduce a double stranded break at the target sequence in the chromosome. Nuclear localization signals are known in the art. See, for example, Makkerh et al. (1996) Current Biology 6:1025-1027.

Cleavage Domain.

A zinc finger nuclease also includes a cleavage domain. The cleavage domain portion of the zinc finger nuclease may be obtained from any endonuclease or exonuclease. Non-limiting examples of endonucleases from which a cleavage domain may be derived include, but are not limited to, restriction endonucleases and homing endonucleases. See, for example, New England Biolabs Catalog or Belfort et al. (1997) Nucleic Acids Res. 25:3379-3388. Additional enzymes that cleave DNA are known (e.g., 51 Nuclease; mung bean nuclease; pancreatic DNase I; micrococcal nuclease; yeast HO endonuclease). See also Linn et al. (eds.) Nucleases, Cold Spring Harbor Laboratory Press, 1993. One or more of these enzymes (or functional fragments thereof) may be used as a source of cleavage domains.

A cleavage domain also may be derived from an enzyme or portion thereof, as described above, that requires dimerization for cleavage activity. Two zinc finger nucleases may be required for cleavage, as each nuclease comprises a monomer of the active enzyme dimer. Alternatively, a single zinc finger nuclease may comprise both monomers to create an active enzyme dimer. As used herein, an "active enzyme dimer" is an enzyme dimer capable of cleaving a nucleic acid molecule. The two cleavage monomers may be derived from the same endonuclease (or functional fragments thereof), or each monomer may be derived from a different endonuclease (or functional fragments thereof).

When two cleavage monomers are used to form an active enzyme dimer, the recognition sites for the two zinc finger nucleases are preferably disposed such that binding of the two zinc finger nucleases to their respective recognition sites places the cleavage monomers in a spatial orientation to each other that allows the cleavage monomers to form an active enzyme dimer, e.g., by dimerizing. As a result, the near edges of the recognition sites may be separated by about 5 to about 18 nucleotides. For instance, the near edges may be separated by about 5, 6, 7, 8, 9, 10, 11, 12, 13, 14, 15, 16, 17 or 18 nucleotides. It will however be understood that any integral number of nucleotides or nucleotide pairs may intervene between two recognition sites (e.g., from about 2 to about 50 nucleotide pairs or more). The near edges of the recognition sites of the zinc finger nucleases, such as for example those described in detail herein, may be separated by 6 nucleotides. In general, the site of cleavage lies between the recognition sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31978-31982. Thus, a zinc finger nuclease may comprise the cleavage domain from at least one Type IIS restriction enzyme and one or more zinc finger binding domains, which may or may not be engineered. Exemplary Type IIS restriction enzymes are described for example in International Publication WO 07/014,275, the disclosure of which is incorporated by reference herein in its entirety. Additional restriction enzymes also contain separable binding and cleavage domains, and these also are contemplated by the present disclosure. See, for example, Roberts et al. (2003) Nucleic Acids Res. 31:418-420.

An exemplary Type IIS restriction enzyme, whose cleavage domain is separable from the binding domain, is FokI. This particular enzyme is active as a dimer (Bitinaite et al. (1998) Proc. Natl. Acad. Sci. USA 95: 10, 570-10, 575). Accordingly, for the purposes of the present disclosure, the portion of the FokI enzyme used in a zinc finger nuclease is considered a cleavage monomer. Thus, for targeted double-stranded cleavage using a FokI cleavage domain, two zinc finger nucleases, each comprising a FokI cleavage monomer, can be used to reconstitute an active enzyme dimer. Alternatively, a single polypeptide molecule containing a zinc finger binding domain and two FokI cleavage monomers can also be used.

In certain embodiments, the cleavage domain comprises one or more engineered cleavage monomers that minimize or prevent homodimerization. By way of non-limiting example, amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains. Exemplary engineered cleavage monomers of FokI that form obligate heterodimers include a pair in which a first cleavage monomer includes mutations at amino acid residue positions 490 and 538 of FokI and a second cleavage monomer that includes mutations at amino-acid residue positions 486 and 499.

Thus, in one embodiment, a mutation at amino acid position 490 replaces Glu (E) with Lys (K); a mutation at amino acid residue 538 replaces Iso (I) with Lys (K); a mutation at amino acid residue 486 replaces Gln (Q) with Glu (E); and a mutation at position 499 replaces Iso (I) with Lys (K). Specifically, the engineered cleavage monomers can be prepared by mutating positions 490 from E to K and 538 from I to K in one cleavage monomer to produce an engineered cleavage monomer designated "E490K:I538K" and by mutating positions 486 from Q to E and 499 from I to L in another cleavage monomer to produce an engineered cleavage monomer designated "Q486E:I499L." The above described engineered cleavage monomers are obligate heterodimer mutants in which aberrant cleavage is minimized or abolished. Engineered cleavage monomers can be prepared using a suitable method, for example, by site-directed mutagenesis of wild-type cleavage monomers (FokI) as described in U.S. Pat. No. 7,888,121, which is incorporated herein in its entirety.

(ii) Optional Polynucleotide

The method for targeted genome editing may further comprise introducing into the cell at least one polynucleotide comprising a sequence having substantial sequence identity to a sequence on at least one side of the targeted cleavage site. For example, the polynucleotide may comprise a first sequence having substantial sequence identity to sequence on one side of the targeted cleavage site and a second sequence having substantial sequence identity to sequence on the other side of the targeted cleavage site. Alternatively, the polynucleotide may comprise a first sequence having substantial sequence identity to sequence on one side of the targeted cleavage site and a second sequence having substantial sequence identity to a sequence located away from the targeted cleavage site. The sequence located away from the targeted cleavage site may be tens, hundreds, or thousands of nucleotides upstream or downstream of the targeted cleavage site.

The lengths of the first and second sequences in the polynucleotide that have substantial sequence identity to sequences in the chromosomal sequence can and will vary. In general, each of the first and second sequences in the polynucleotide are at least about 10 nucleotides in length. In various embodiments, the polynucleotide sequences having substantial sequence identity with chromosomal sequences are about 15 nucleotides, about 20 nucleotides, about 25 nucleotides, about 30 nucleotides, about 40 nucleotides, about 50 nucleotides, about 100 nucleotides, or more than 100 nucleotides in length.

The phrase "substantial sequence identity" means that the sequences in the polynucleotide have at least about 75% sequence identity with the chromosomal sequences of interest. In some embodiments, the sequences in the polynucleotide have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with the chromosomal sequence of interest.

The length of the polynucleotide can and will vary. For example, the polynucleotide may range from about 20 nucleotides in length up to about 200,000 nucleotides in length. In various embodiments, the polynucleotide ranges from about 20 nucleotides to about 100 nucleotides in length, from about 100 nucleotides to about 1000 nucleotides in length, from about 1000 nucleotides to about 10,000 nucleotides in length, from about 10,000 nucleotides to about 100,000 nucleotides in length, or from about 100,000 nucleotides to about 200,000 nucleotides in length.

Typically, the polynucleotide will be DNA. The DNA may be single-stranded or double-stranded. The donor polynucleotide may be a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer.

In some embodiments, the polynucleotide may further comprise a marker. Non-limiting examples of suitable markers include restriction sites, fluorescent proteins, or selectable markers. Such markers enable screening for targeted integrations.

(iii) Introducing into the Cell

The targeting endonuclease can be introduced into the cell as a protein or as a nucleic acid that encodes the targeting endonuclease. The nucleic acid encoding the targeting endonuclease may be DNA or RNA (i.e., mRNA). In embodiments in which the encoding nucleic acid is mRNA, the mRNA may be 5' capped and/or 3' polyadenylated. In embodiments in which the encoding nucleic acid is DNA, the DNA may be linear or circular. The DNA may be part of a vector, wherein the encoding DNA is optionally operably linked to a suitable promoter. Those skilled in the art are familiar with appropriate vectors, promoters, other control elements, and means of introducing the vector into the cell of interest.

The targeting endonuclease or nucleic acid encoding the targeting endonuclease and the optional polynucleotide described above can be introduced into the cell by a variety of means. Suitable delivery means include microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In certain embodiments, the targeting endonuclease molecule and optional polynucleotides are introduced into a cell by nucleofection or electroporation.

In embodiments in which more than one targeting endonuclease molecule and more than one polynucleotide are introduced into a cell, the molecules can be introduced simultaneously or sequentially. For example, targeting endonuclease molecules, each specific for a targeted cleavage site (and optional polynucleotides) can be introduced at the same time. Alternatively, each targeting endonuclease molecule, as well as the optional polynucleotides(s) can be introduced sequentially.

The ratio of the targeting endonuclease (or encoding nucleic acid) molecule to the optional polynucleotide can and will vary. In general, the ratio of targeting endonuclease molecule to polynucleotide may range from about 1:10 to about 10:1. In various embodiments, the ratio of the targeting endonuclease molecule to polynucleotide is about 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1. In one embodiment, the ratio is about 1:1.

(b) RNA Interference

In another embodiment, the cell line deficient in Cmah and/or Ggta1 can be prepared using an RNA interference (RNAi) agent that inhibits expression of a target mRNA or transcript. The RNAi agent may lead to cleavage of the target mRNA or transcript. Alternatively, the RNAi agent may prevent or disrupt translation of the target mRNA into protein.

In some embodiments, the RNAi agent may be a short interfering RNA (siRNA). In general, a siRNA comprises a double-stranded RNA molecule that ranges from about 15 to about 29 nucleotides in length. The siRNA may be about 16-18, 17-19, 21-23, 24-27, or 27-29 nucleotides in length. In a specific embodiment, the siRNA is about 21 nucleotides in length. The siRNA may optionally further comprise one or two single-stranded overhangs, e.g., a 3' overhang on one or both ends. The siRNA may be formed from two RNA molecules that hybridize together or, alternatively, may be generated from a short hairpin RNA (shRNA) (see below). In some embodiments, the two strands of the siRNA are completely complementary, such that no mismatches or bulges exist in the duplex formed between the two sequences. In other embodiments, the two strands of the siRNA are substantially complementary, such that one or more mismatches and/or bulges may exist in the duplex formed between the two sequences. In certain embodiments, one or both of the 5' ends of the siRNA have a phosphate group, while in other embodiments one or both of the 5' ends lack a phosphate group. In other embodiments, one or both of the 3' ends of the siRNA have a hydroxyl group, while in other embodiments one or both of the 5' ends lack a hydroxyl group.

One strand of the siRNA, which is referred to as the "antisense strand" or "guide strand," includes a portion that hybridizes with the target transcript. In certain embodiments, the antisense strand of the siRNA is completely complementary with a region of the target transcript, i.e., it hybridizes to the target transcript without a single mismatch or bulge over a target region between about 15 and about 29 nucleotides in length, preferably at least 16 nucleotides in length, and more preferably about 18-20 nucleotides in length. In other embodiments, the antisense strand is substantially complementary to the target region, i.e., one or more mismatches and/or bulges may exist in the duplex formed by the antisense strand and the target transcript. Typically, siRNAs are targeted to exonic sequences of the target transcript. Those of skill in the art are familiar with programs, algorithms, and/or commercial services that design siRNAs for target transcripts. An exemplary example is the Rosetta siRNA Design Algorithm (Rosetta Inpharmatics, North Seattle, Wash.) and MISSION® siRNA (Sigma-Aldrich, St. Louis, Mo.). The siRNA can be enzymatically synthesized in vitro using methods well known to those of skill in the art. Alternatively, the siRNA can be chemically synthesized using oligonucleotide synthesis techniques that are well known in the art.

In other embodiments, the RNAi agent may be a short hairpin RNA (shRNA). In general, a shRNA is an RNA molecule comprising at least two complementary portions that are hybridized or are capable of hybridizing to form a double-stranded structure sufficiently long to mediate RNA interference (as described above), and at least one single-stranded portion that forms a loop connecting the regions of the shRNA that form the duplex. The structure may also be called a stem-loop structure, with the stem being the duplex portion. In some embodiments, the duplex portion of the structure is completely complementary, such that no mismatches or bulges exist in the duplex region of the shRNA. In other embodiments, the duplex portion of the structure is substantially complementary, such that one or more mismatches and/or bulges exist in the duplex portion of the shRNA. The loop of the structure may be from about 1 to about 20 nucleotides in length, preferably from about 4 to about 10 about nucleotides in length, and more preferably from about 6 to about 9 nucleotides in length. The loop may be located at either the 5' or 3' end of the region that is complementary to the target transcript (i.e., the antisense portion of the shRNA).

The shRNA may further comprise an overhang on the 5' or 3' end. The optional overhang may be from about 1 to about 20 nucleotides in length, and more preferably from about 2 to about 15 nucleotides in length. In some embodiments, the overhang comprises one or more U residues, e.g., between about 1 and about 5 U residues. In some embodiments, the 5' end of the shRNA has a phosphate group, while in other embodiments it does not. In other embodiments, the 3' end of the shRNA has a hydroxyl group, while in other embodiments it does not. In general, shRNAs are processed into siRNAs by the conserved cellular RNAi machinery. Thus, shRNAs are precursors of siRNAs and are similarly capable of inhibiting expression of a target transcript that is complementary of a portion of the shRNA (i.e., the antisense portion of the shRNA). Those of skill in the art are familiar with the available resources (as detailed above) for the design and synthesis of shRNAs. An exemplary example is MISSION® shRNAs (Sigma-Aldrich).

In still other embodiments, the RNAi agent may be an RNAi expression vector. Typically, an RNAi expression vector is used for intracellular (in vivo) synthesis of RNAi agents, such as siRNAs or shRNAs. In one embodiment, two separate, complementary siRNA strands are transcribed using a single vector containing two promoters, each of which directs transcription of a single siRNA strand (i.e., each promoter is operably linked to a template for the siRNA so that transcription may occur). The two promoters may be in the same orientation, in which case each is operably linked to a template for one of the complementary siRNA strands. Alternatively, the two promoters may be in opposite orientations, flanking a single template so that transcription for the promoters results in synthesis of two complementary siRNA strands. In another embodiment, the RNAi expression vector may contain a promoter that drives transcription of a single RNA molecule comprising two complementary regions, such that the transcript forms a shRNA.

Those of skill in the art will appreciate that it is preferable for siRNA and shRNA agents to be produced in vivo via the transcription of more than one transcription unit. Generally speaking, the promoters utilized to direct in vivo expression of the one or more siRNA or shRNA transcription units may be promoters for RNA polymerase III (Pol III). Certain Pol III promoters, such as U6 or H1 promoters, do not require cis-acting regulatory elements within the transcribed region, and thus, are preferred in certain embodiments. In other embodiments, promoters for Pol II may be used to drive expression of the one or more siRNA or shRNA transcription units. In some embodiments, tissue-specific, cell-specific, or inducible Pol II promoters may be used.

A construct that provides a template for the synthesis of siRNA or shRNA may be produced using standard recombinant DNA methods and inserted into any of a wide variety of different vectors suitable for expression in eukaryotic cells. Recombinant DNA techniques are described in Ausubel et al, supra and Sambrook & Russell, supra. Those of skill in the art also appreciate that vectors may comprise additional regulatory sequences (e.g., termination sequence, translational control sequence, etc.), as well selectable marker sequences. DNA plasmids are known in the art, including those based on pBR322, PUC, and so forth. Since many expression vectors already contain a suitable promoter or promoters, it may be only necessary to insert the nucleic acid sequence that encodes the RNAi agent of interest at an appropriate location with respect to the promoter(s). Viral vectors may also be used to provide intracellular expression of RNAi agents. Suitable viral vectors include retroviral vectors, lentiviral vectors, adenoviral vectors, adeno-associated virus vectors, herpes virus vectors, and so forth. In a specific embodiment, the RNAi expression vector is a shRNA lentiviral-based vector or lentiviral particle, such as that provided in MISSION® TRC shRNA products (Sigma-Aldrich).

The RNAi agents or RNAi expression vectors ca be introduced into the cell using methods well known to those of skill in the art. Such techniques are described in Ausubel et al., supra or Sambrook & Russell, supra, for example. In certain embodiments, the RNAi expression vector, e.g., a viral vector, is stably integrated into the genome of the cell, such that Cmah and/or Ggta1 expression is disrupted over subsequent cell generations.

(c) Random Mutagenesis

In still other embodiments, the cell line deficient in Cmah and/or Ggta1 can be prepared using random mutagenesis. In one embodiment, a random mutation is generated by exposing the cell to a chemical such as N-ethyl-N-nitrosourea (ENU), N-ethyl-N-nitrosourea (NMU), ethyl methanesulfonate (EMS), nitrous acid (NA), or another mutagenic chemical. In another embodiment, a random mutation is generated using a transposon-based system to randomly insert short sequences in the genome, thereby disrupting expression of the chromosomal sequence in which a sequence is inserted. In another embodiment, a random mutation is generated using ionizing radiation.

(d) Site-Specific Recombination

In alternate embodiments, the cell line deficient in Cmah and/or Ggta1 can be prepared using site-specific recombination techniques. For example, site-specific recombination techniques can be used to delete all or part of a chromosomal sequence of interest, or introduce single nucleotide polymorphisms (SNPs) into the chromosomal sequence of interest. In one embodiment, the chromosomal sequence of interest is targeted using a Cre-IoxP site-specific recombination system, a Flp-FRT site-specific recombination system, or variants thereof. Such recombination systems are commercially available, and additional teaching for these techniques is found in Ausubel et al., supra, for example.

(III) Methods for Producing Recombinant Proteins

A further aspect of the present disclosure encompasses a method for producing a recombination protein with a human-like glycosylation pattern. In general, a glycoprotein having a human-like glycosylation pattern lacks α-Gal and/or Neu5Gc residues. The method comprises expressing the recombination protein in a non-human mammalian cell line deficient in Cmah and/or Ggta1. Cell lines deficient in Cmah and/or Ggta1 are described above in section (I).

In one exemplary embodiment, the cell line may comprise a biallelic inactivation of the chromosomal sequence encoding Cmah such that the cell line produces no Cmah and the recombinant protein produced by the cell line lacks α-Gal moieties. In another exemplary embodiment, the cell line may comprise a biallelic inactivation of the chromosomal sequence encoding Ggta1 such that the cell line produces no Ggta1 and the recombinant protein produced by the cell line lacks Neu5Gc residues. In a further exemplary embodiment, the cell line may comprise biallelic inactivations of the chromosomal sequences encoding Cmah and Ggta1 such that the cell line produces no Cmah or Ggta1 and the recombinant protein produced by the cell lacks α-Gal and Neu5Gc residues. In another embodiment, in which the cell line is aneuploid, all copies of the chromosomal sequence encoding Cmah are inactivated such that the cell line produces no Cmah and the recombinant protein produced by the cell line lacks α-Gal moieties. In another exemplary embodiment, in which the cell line is aneuploid, all copies of the chromosomal sequence encoding Ggta1 are inactivated such that the cell line produces no Ggta1 and the recombinant protein produced by the cell line lacks Neu5Gc residues. In a further exemplary embodiment, in which the cell line is aneuploid, all copies of the chromosomal sequence encoding Cmah and all copies of the chromosomal sequence encoding Ggta1 are inactivated such that the cell line produces no Cmah or Ggta1 and the recombinant protein produced by the cell lacks α-Gal and Neu5Gc residues.

In general, the recombinant protein produced by the cell line deficient in Cmah and/or Ggta1 has at least one property that is improved relative to the same protein produced by a comparable cell line that is not deficient in Cmah and/or Ggta1. Non-limiting examples of improved properties include reduced immunogenicity, increased bioavailability, increased efficacy, increased stability, increased solubility, improved half-life, improved clearance, improved pharmacokinetics, and combinations thereof. For example, because the recombinant protein produced by the method disclosed herein lacks α-Gal and/or Neu5Gc residues, the recombinant protein produced has reduced immunogenicity and reduced potential for inducing hypersensitive reactions in human subjects than a comparable protein containing α-Gal and/or Neu5Gc residues.

The recombinant protein produced in the cell line deficient in Cmah and/or Ggta1 can be any suitable protein, including therapeutic proteins and protein biologics. For example, the recombinant protein may be, without limit, an antibody, a fragment of an antibody, a monoclonal antibody, a humanized antibody, a humanized monoclonal antibody, a chimeric antibody, an IgG molecule, an IgG heavy chain, an IgG light chain, an IgA molecule, an IgD molecule, an IgE molecule, an IgM molecule, a glycoprotein, a growth factor, a cytokine, an interferon, an interleukin, a hormone, a clotting (or coagulation) factor, a blood component, an enzyme, a nutraceutical protein, a vaccine, a functional fragment or functional variant of any of the forgoing, or a fusion protein comprising any of the foregoing proteins and/or functional fragments or variants thereof.

Methods for producing recombinant protein are well known in the art, and additional teaching is provided by Ausubel et al., supra. In general, the recombinant protein is expressed from an exogenously introduced nucleic acid. As detailed above in section (I)(a), the nucleic acid encoding the recombinant protein may be extrachromosomal or the nucleic acid encoding the recombinant protein may be integrated into the genome.

Methods for culturing the cell line such that the recombinant protein is expressed are well known in the art. Appropriate media and culture systems are known in the art and commercially available. In one embodiment, the recombinant protein is produced by the cell lines disclosed herein via serum free suspension culture.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As used herein, the term "endogenous sequence" refers to a chromosomal sequence that is native to the cell.

The term "exogenous sequence" refers to a chromosomal sequence that is not native to the cell, or a chromosomal sequence whose native location is in a different chromosomal location.

The terms "editing," "genome editing," or "chromosomal editing" refer to a process by which a specific chromosomal sequence is changed. The edited chromosomal sequence may comprise an insertion of at least one nucleotide, a deletion of at least one nucleotide, and/or a substitution of at least one nucleotide.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The term "heterologous" refers to an entity that is not native to the cell or species of interest.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues.

The term "recombination" refers to a process of exchange of genetic information between two polynucleotides. For the purposes of this disclosure, "homologous recombination" refers to the specialized form of such exchange that takes place, for example, during repair of double-strand breaks in cells. This process requires sequence similarity between the two polynucleotides, uses a "donor" or "exchange" molecule to template repair of a "target" molecule (i.e., the one that experienced the double-strand break), and is variously known as "non-crossover gene conversion" or "short tract gene conversion," because it leads to the transfer of genetic information from the donor to the target. Without being bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized homologous recombination often results in an alteration of the sequence of the target molecule such that part or all of the sequence of the donor polynucleotide is incorporated into the target polynucleotide.

As used herein, the terms "target site" or "target sequence" refer to a nucleic acid sequence that defines a portion of a chromosomal sequence to be edited and to which a targeting endonuclease is engineered to recognize, bind, and cleave.

The terms "upstream" and "downstream" refer to locations in a nucleic acid sequence relative to a fixed position. Upstream refers to the region that is 5' (i.e., near the 5' end of the strand) to the position and downstream refers to the region that is 3' (i.e., near the 3' end of the strand) to the position.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. 0. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

As various changes could be made in the above-described cells and methods without departing from the scope of the invention, it is intended that all matter contained in the above description and in the examples given below, shall be interpreted as illustrative and not in a limiting sense.

EXAMPLES

The following examples illustrate certain aspects of the invention.

Example 1

CHO Cells Contain Ggta1 Gene

To confirm the presence of the Ggta1 gene in CHO K1 cells, primers were designed to amplify regions of exons 8 and 9 of the Ggta1 gene. DNA from murine myeloma NS0 and CHO K1 cells was PCR amplified using one pair of primers. A band of the expected size of about 300 bp was detected in both NS0 and CHO cells. The PCR fragments isolated from CHO cells were sequenced and aligned with the mouse Ggta1 gene (UniProtKB/Swiss-Prot Accession No.: P23336). Sequence identity was approximately 85%.

Quantitative PCR was used to evaluate mRNA expression in CHO cells relative to mouse cells. After normalization using actin, a comparison of the threshold cycle (Ct) values between the mouse NS0 cells and the CHO cells suggested that Ggta1 expression was significantly lower in CHO cells that in NS0 cells.

Example 2

Generation of CHO Cells Comprising an Inactivated Ggta1 Locus

A pair of ZFNs was designed to target a region within exon 9 of the Ggta1 gene in CHO cells. Ggta1 sequences were obtained from a proprietary transcriptome sequence and verified using RT-PCR. ZFNs targeting the gene were designed using a proprietary algorithm, and subsequently tested. In vitro transcription and mRNA poly-adenylation and capping were produced from ZFN plasmid DNA as described in CompoZr® Knockout Zinc Finger Nucleases (ZFN) product information. Briefly, plasmid ZFN DNA was linearized, and purified via phenol/chloroform DNA extraction. MessageMax™ T7 ARCA-Capped Message Transcription Kit (Cell Script Inc.) was used to cap the linearized DNA. A Poly(A) Polymerase Tailing Kit (EpiCenter) was used to add a poly (A) tail. ZFN mRNA was purified using the MEGAclear™ kit (Ambion).

The CHOZN (gs−/−) cell line expressing recombinant anti-Rabies human IgG was used. All cell culture media, supplements and other reagents used were purchased from Sigma-Aldrich unless otherwise specified. Prior to transfection, cells were maintained as suspension cultures in EX-CELL® CHO CD Fusion (Sigma-Aldrich) supplemented with 6 mM L-glutamine. Cells were seeded at $0.5 \times 10^6$ cells/mL in bioreactor tubes one day prior to transfection. For each transfection, $1 \times 10^6$ cells in 150 µL growth media and 54 each ZFN mRNA were used. Transfections were conducted by electroporation at 140 V and 950 µF in 0.2 cm cuvettes. Electroporated cells were placed in 2 mL growth media in a 6-well plate static culture. Control cells were mock transfected.

Figure 1:
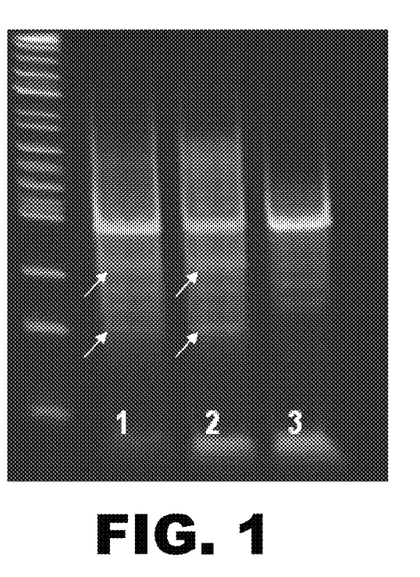
FIG. 1 illustrates ZFN-mediated cleavage of the Ggta1 locus in CHO cells. Shown are the results of a Cel-1 surveyor nuclease assay. Arrows denote 215 bp and 100 bp cleavage products in CHO cells transfected with ZFN mRNA (1) or ZFN DNA (2). No cleavage products were detected in mock transfected cells (3).

On days 3 and 10 post-transfection, cells were removed from culture and genomic DNA was isolated using Sigma-Aldrich GeneElute Mammalian Genomic DNA Miniprep Kit. ZFN-induced cleavage was verified using a Cel-1 nuclease assay, as described in CompoZr® Knockout ZFN product information. This assay is conducted to determine the efficiency of ZFN-mediated gene mutation as described previously (Miller J C et al., Nat. Biotechnol. 2007, 25:778-785). The assay detects alleles of the targeted locus that deviate from wild type as a result of non-homologous end joining (NHEJ)-mediated imperfect repair of ZFN-induced DNA double strand breaks. PCR amplification of the targeted region from a pool of ZFN-treated cells generates a mixture of wild type (WT) and mutant amplicons. Melting and reannealing of this mixture results in mismatches forming between heteroduplexes of the WT and mutant alleles. A DNA "bubble" formed at the site of mismatch is cleaved by the surveyor nuclease Cel-1, and the cleavage products can be resolved by gel electrophoresis. As shown in FIG. 1, two fragments of about 215 bp and 100 bp were present in the ZFN transfected cells (lanes 1 and 2) but absent in the mock transfected control cells.

Example 3

Single Cell Cloning and Genotyping of Ggta1 Knockout Cells

Upon confirmation of ZFN activity using the Cell assay, the Ggta1 ZFN transfected cells were single-cell cloned using limiting dilution. For this, cells were plated at 0.5 cell/well using a mixture of 80% CHO serum-free cloning media, 20% conditioned media, and 4 mM L-glutamine. Clonality and growth were microscopically verified on days 7 and 14 post plating, respectively. Clones with growth were expanded and genotyped by PCR and sequencing. One Ggta1 (−/−) and four Ggta1 (+/−) clones were isolated that bore deletions of various lengths, as detailed below in Table 1. All of the cell lines exhibited similar growth characteristics as the parental cell line from which they were derived.

TABLE 1

Genotypic characterization of Ggta1 knockout clones

| Clone ID | Allele 1 | Allele 2 | Genotype |
|---|---|---|---|
| BF10 | 14 bp deletion | Not detected | Biallelic knockout |
| CG3 | 7 bp deletion | wildtype | Heterozygote |
| DA4 | 2 bp deletion | wildtype | Heterozygote |
| DC7 | 11 bp deletion | wildtype | Heterozygote |
| DG5 | 6 bp deletion + 2 bp deletion | wildtype | Heterozygote |

Example 4

Generation of CHO Cells Comprising an Inactivated Cmah Locus

A pair of ZFNs was designed to target a region within exon 5 of the Cmah locus in CHO cells (UniProtKB/Swiss-Prot Accession No.: Q9WV23; Chinese hamster). The CHO K1 cell line was transfected with 20 µg RNA encoding the ZFNs using standard procedures and methods similar to those described in Example 2. Control cells were transfected with RNA encoding GFP.

Figure 2:
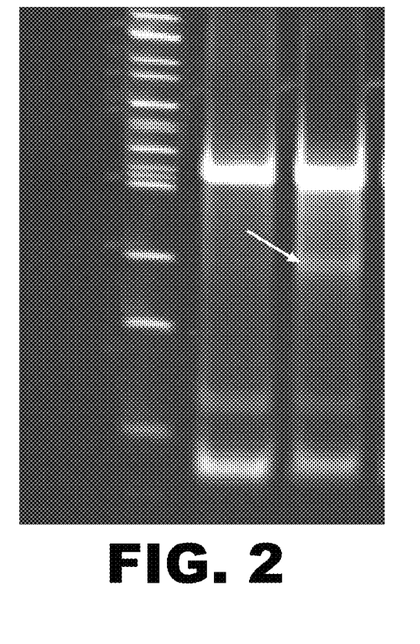
FIG. 2 documents ZFN-mediated cleavage of the Cmah locus in CHO cells, as detected by a Cel-1 surveyor nuclease assay. Arrow denotes a cleavage product.

The efficiency of ZFN-induced double strand chromosomal breaks was determined using the Cel-1 nuclease assay. As shown in FIG. 2, the Cmah ZFNs cleaved the Cmah target in CHO cells. The frequency of ZFN-mediated cleavage can be estimated by comparing the relative intensity of the cleavage products to the relative intensity of the parental band. The frequency of cleavage was calculated by the ImageJ software to be about 11%.

Example 5

Single Cell Cloning and Genotyping of Cmah Knockout Cells

The Cmah ZFN transfected cells were single-cell cloned using limiting dilution (as described above) or Fluorescence Activated Cell Sorting (FACS). Clones with growth were expanded and genotyped by PCR and sequencing. Genotyping revealed that all 20 clones from this round of work were Cmah (+/−) that bore deletions and insertions of various lengths. Subsequently, seven Cmah (+/−) clones were pooled, and re-transfected with Cmah ZFN RNA, and single-cell cloned by limiting dilution. Six clones from the second round of work were verified by PCR and sequencing to be Cmah (−/−). The inactivated Cmah loci bore deletions and insertions of various lengths (see Table 2). The genotypes of these Cmah biallelic knockout cell lines are also listed in Table 2. All cell lines exhibited growth characteristics that were similar to those of the parental cell line from which they were derived.

TABLE 2

Genotypic characterization of Cmah (−/−) clones

| Clone ID | Allele 1 | Allele 2 | Genotype |
|---|---|---|---|
| AB10 | 5 bp insertion | 12 bp deletion | Biallelic knockout |
| AB2 | 17 bp deletion | 31 bp deletion | Biallelic knockout |
| BA4 | 17 bp deletion | 33 bp deletion | Biallelic knockout |
| BD10 | 12 bp deletion | 12 bp deletion | Biallelic knockout |
| BF3 | 20 bp insertion | 4 bp deletion | Biallelic knockout |
| BG11 | 4 bp insertion | 17 bp deletion | Biallelic knockout |

Example 6

Generation of Cmah/Ggta1 Double Knockout Cells

Figure 3:
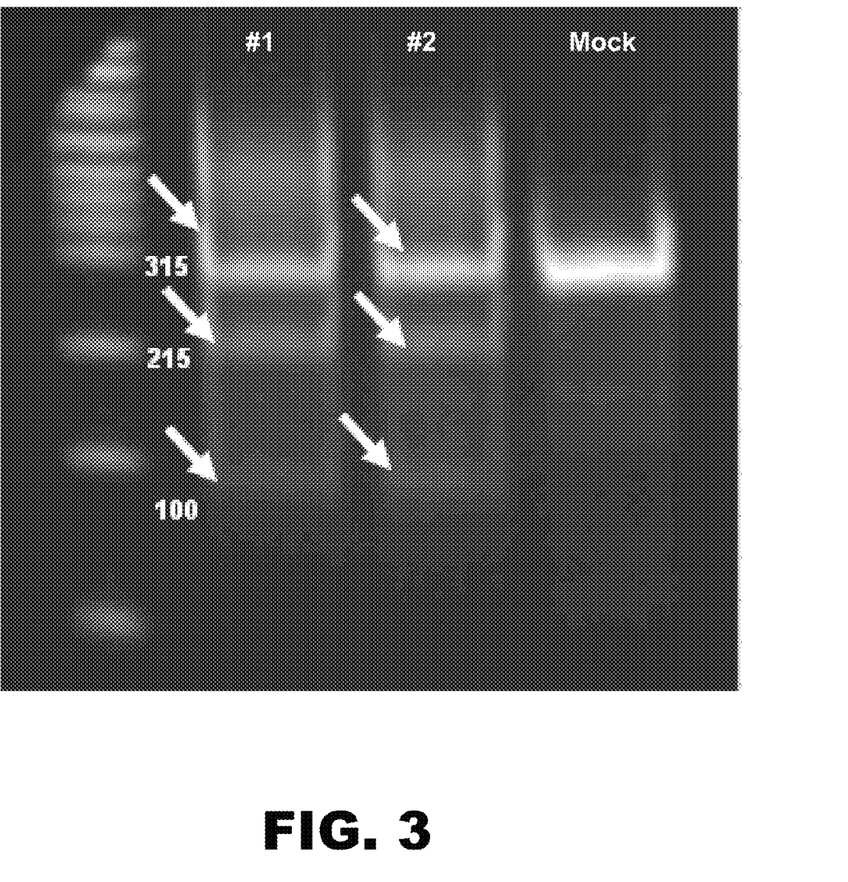
FIG. 3 illustrates ZFN-mediated cleavage of the Ggta1 locus in Cmah (−/−) cells, as detected by a Cel-1 surveyor nuclease assay. The ZFN-transfected cells (marked "#1" and "#2") but not the mock transfected cells had the 215 bp and 100 bp cleavage fragments.

A clonal cell line with a confirmed Cmah (−/−) genotype (i.e., AB2) was transfected with ZFNs targeting Ggta1 essentially as described above in Example 2. ZFN activity was confirmed using the Cel-1 nuclease assay. As shown in FIG. 3, cleavage products were detected in the ZFN-transfected cells but not the mock transfected cells.

The cells were single cell cloned using limiting dilution essentially as described above in Example 3. Nested PCR was performed on 192 clones, and 26 clones were identified as potential double knockout clones based on the size of the PCR product. Genomic DNA was isolated from the potential double knockout clones, PCR amplified, and sequenced. Four clones had 2× sequence coverage confirming the biallelic deletion of Ggta1 in the Cmah knockout background. Table 3 presents the genotypes of the Cmah (−/−)/Ggta1 (−/−) double knockout clones.

TABLE 3

Genotypic characterization of Cmah/Ggta1 double knockout clones

| Clone # | Cmah alleles | Ggta1 alleles | Genotype |
|---|---|---|---|
| 8 | 1. 17 bp deletion<br>2. 31 bp deletion | 1. 4 bp deletion<br>2. 4 bp deletion | Biallelic double knockout |
| 19 | 1. 17 bp deletion<br>2. 31 bp deletion | 1. 3 bp deletion<br>2. 3 bp deletion | Biallelic double knockout |
| 17 | 1. 17 bp deletion<br>2. 31 bp deletion | 1. 4 bp deletion<br>2. 4 bp deletion | Biallelic double knockout |
| 1 | 1. 17 bp deletion<br>2. 31 bp deletion | 1. 23 bp deletion<br>2. 23 bp deletion | Biallelic double knockout |

What is claimed is:

1. A method for producing a recombinant protein with a human-like glycosylation pattern, the method comprising expressing the recombinant protein in a Chinese Hamster Ovary cell (CHO) cell line deficient in glutamine synthase, cytidine monophosphate-N-acetylneuraminic acid hydroxylase (Cmah) and glycoprotein alpha-1,3-galactosyltransferase-1 (Ggta1).

2. The method of claim 1, wherein the cell line comprises an inactivated chromosomal sequence encoding Cmah and an inactivated chromosomal sequence encoding Ggta1, and the cell line produces a reduced amount of Cmah and Ggta1.

3. The method of claim 2, wherein the recombinant protein has a reduced content of N-glycolylneuraminic acid (Neu5Gc) residues and galactosealpha-1,3-galactose (alpha-Gal) residues compared to the same recombinant protein produced by a comparable cell line not deficient in Cmah and/or Ggta1.

4. The method of claim 2, wherein all copies of the chromosomal sequence encoding Cmah and/or Ggta1 are inactivated, and the cell line produces no Cmah and/or Ggta1.

5. The method of claim 4, wherein the recombinant protein lacks N-glycolylneuraminic acid (Neu5Gc) residues and galactose-alpha-1,3-galactose (alpha-Gal) residues.

6. The method of claim 1, wherein the recombinant protein has at least one property that is improved relative to the same recombinant protein produced by a comparable cell line not deficient in Cmah and/or Ggta1.

7. The method of claim 6, wherein the property that is improved is chosen from reduced immunogenicity, increased bioavailability, increased efficacy, increased stability, increased solubility, improved half-life, improved clearance, or improved pharmacokinetics.

8. The method of claim 1, wherein the recombinant protein is chosen from an antibody, an antibody fragment, a growth factor, a cytokine, a hormone, and a clotting factor.

9. The method of claim 1, wherein all copies of the chromosomal sequence encoding Cmah are inactivated, the cell line produces no Cmah, and the recombinant protein lacks Neu5Gc residues.

10. The method of claim 1, all copies of the chromosomal sequence encoding Ggta1 are inactivated, the cell line produces no Ggta1, and the recombinant protein lacks alpha-Gal residues.

11. The method of claim 1, wherein, all copies of the chromosomal sequence encoding Cmah and all copies of chromosomal sequence encoding Ggta1 are inactivated, the cell line produces no Cmah or Ggta1, and the recombinant protein lacks Neu5Gc and alpha-Gal residues.

* * * * *